(12) United States Patent
Richter et al.

(10) Patent No.: US 7,276,604 B2
(45) Date of Patent: Oct. 2, 2007

(54) CRYSTALLINE FORM OF THE SODIUM SALT OF 3-PYRIDYL-1-HYDROXYETHYLI-DENE-1,1-BISPHOSPHONIC ACID

(75) Inventors: Jindrich Richter, Pradubice (CZ); Josef Jirman, Prague (CZ)

(73) Assignee: Zentiva A.S., Prague (CZ)

( * ) Notice: Subject to any disclaimer, the term of this patent is extended or adjusted under 35 U.S.C. 154(b) by 7 days.

(21) Appl. No.: 10/531,877

(22) PCT Filed: Oct. 21, 2003

(86) PCT No.: PCT/CZ03/00056

§ 371 (c)(1),
(2), (4) Date: Aug. 1, 2005

(87) PCT Pub. No.: WO2004/037252

PCT Pub. Date: May 6, 2004

(65) Prior Publication Data

US 2006/0148762 A1    Jul. 6, 2006

(30) Foreign Application Priority Data

Oct. 25, 2002   (CZ) .......................... PV 2002-3574

(51) Int. Cl.
C07D 213/24   (2006.01)
A61K 31/66   (2006.01)
(52) U.S. Cl. .......................... 546/22; 514/89
(58) Field of Classification Search .................. 514/89; 546/22
See application file for complete search history.

(56) References Cited

U.S. PATENT DOCUMENTS

2006/0148762 A1    7/2006   Richter et al.

FOREIGN PATENT DOCUMENTS

| WO | 01/56983 | 8/2001 |
|---|---|---|
| WO | 03/086355 | 10/2003 |

OTHER PUBLICATIONS

Gossman, William L. et al.: "Three hydrates of the bisphosphonate risedronate, consisting of one molecular and two ionic structures", Acta Crystallographica Section C, vol. C59, pp. m33-m36, Jan. 11, 2003.
Kushida, K.: "Sodium risedronate hydrate", Rinsho To Yakubutsu Chiryo, vol. 21, No. 10, pp. 1040-1041, 2002. XP001157194.
Redman-Furey, Nancy L. et al.: "Thermoanalytical Characterization of the Hydration States of Risedronate", Proceedings of the NATAS Annual Conference on Thermal Analysis and Applications, No. 30th, pp. 733-738, Sep. 21-22, 2002. XP009024613.
U.S. Appl. No. 10/590,694, filed Aug. 25, 2006, Richter et al.

*Primary Examiner*—Charanjit S. Aulakh
(74) *Attorney, Agent, or Firm*—Oblon, Spivak, McClelland, Maier & Neustadt, P.C.

(57) ABSTRACT

The present invention relates to a crystalline, hydrated form of the sodium salt of 3-pyridyl-1-hydroxyethylidene-1,1-bisphosphonic acid. The hydrate contains from 6.4 up to 22 weight % of sodium and 15 up to 23 weight % of crystalline water if the sodium content is lower than 7.5 weight %, based on the whole molecule, or 4.5 up to 18 weight % of crystalline water if the sodium content is equal to or higher than 13 weight %, based on the anhydrous substance. Due to stability in humid environments, the hydrate is useful as an active substance for the treatment of diseases associated with bone resorption disorders.

11 Claims, 8 Drawing Sheets

CRYSTALLINE FORM OF THE SODIUM SALT OF 3-PYRIDYL-1-HYDROXYETHYLIDENE-1,1-BISPHOSPHONIC ACID

TECHNICAL FIELD

The invention concerns new crystalline hydrates of 3-pyridyl-1-hydroxyethylidene-1,1-bisphosphonic acid of formula

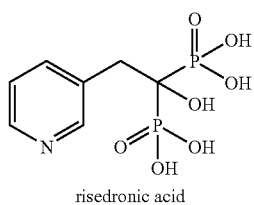

risedronic acid and its salts, resp., and a method of their production.

BACKGROUND ART

Geminal bisphosphonates, such as for example salts of 3-pyridyl-1-hydroxyethylidene-1,1-bisphosphonic acid (risedronate) or 4-amino-1-hydroxybutylidene-1,1-bisphosphonic acid (alendronate), have been used for quite some time to treat bone diseases and for management of the metabolism of calcium.

Preparation of risedronic acid consists in reaction of 3-pyridylacetic acid with phosphoric and phosphorus trichloride with subsequent hydrolysis of resulting intermediates. The general method of this preparation of bisphosphonic acids was mentioned in JP 80-98193 (1980), JP 80-98105 (1980) of Nissan Chemical Industries and in an article W. Ploger et al., Z. Anorg. Allg. Chem., 389,119, (1972). A preparation of risedronate was published in EP 186405 (1986) of Procter & Gamble.

Bisphosphonic acids are used in the form of various non-toxic and pharmaceutically acceptable esters, alkali metal salts and salts of alkaline-earth metals and their various hydrates. The form of the substance can have a fundamental influence on its solubility and its biological availability. The preferred forms of risedronate are the sodium and calcium salts.

3-pyridyl-1-hydroxyethylidene-1,1-bisphosphonic acid is used mainly in the form of its mono-sodium salt (sodium risedronate). This salt, similarly as a number of other geminal bisphosphonic acids and their salts, is capable of forming hydrates. So far, anhydrous crystalline form of mono-sodium 3-pyridyl-1-hydroxyethylidene-1,1-bisphosphonate, its monohydrate and pentahemihydrate have been described in the application WO 0156983 A2 of Procter & Gamble. Of the two mentioned hydrates, only the pentahemihydrate form is thermodynamically stable. The monohydrate undergoes a spontaneous transformation to the stable pentahemihydrate.

A disadvantage of lower hydrates or anhydrous forms of monosodium 3-pyridyl-1-hydroxyethylidene-1,1-bisphosphonate is their hygroscopicity and related instability of the content of the active substance. A decrease of the active substance content with time translates into the substance's limited storage time. Hygroscopicity can also lead to instability of a pharmaceutical preparation. For example, tablets can disintegrate under the influence of air humidity.

In case of a pharmaceutical preparation containing a mixture of the monohydrate and hemipentahydrate of monosodium 3-pyridyl-1-hydroxyethylidene-1,1-bisphosphonate, as it is described in WO 0156983, especially the monohydrate, which is known not to be thermodynamically stable, can be a source of instability.

Solutions involving double or hermeneutically sealed packaging, or addition of a desiccant into the package, always result in additional production costs.

The present invention, which concerns new stable hydrates of the sodium salts of 3-pyridyl-1-hydroxyethylidene-1,1-bisphosphonic acid, solves this problem. These hydrates are, in addition, better soluble in diluted hydrochloric acid, which makes up stomach juices.

DISCLOSURE OF INVENTION

Definitions of the terms used in the description of this invention:

The term risedronic acid refers to 3-pyridyl-1-hydroxyethylidene-1,1-bisphosphonic acid.

The term risedronate stands for both risedronic acid and its pharmaceutically acceptable salts.

The term risedronate sodium salt monohydrate refers to a crystalline form of monosodium 3-pyridyl-1-hydroxyethylidene-1,1-bisphosphonate which contains from 5 to 7.1 w. % of water and from 5.5 to 7.5% of sodium based on the anhydrous salt.

The term risedronate sodium salt pentahemihydrate stands for a crystalline form of monosodium 3-pyridyl-1-hydroxyethylidene-1,1-bisphosphonate which contains from 11.9 to 13.9 w. % of water and from 5.5 to 7.5% of sodium based on the anhydrous salt.

The term risedronate sodium salt pentahydrate stands for a crystalline form of monosodium 3-pyridyl-1-hydroxyethylidene-1,1-bisphosphonate which contains from 20 to 23 w. % of water and from 5.5 to 7.5% of sodium based on the anhydrous salt.

The term risedronate disodium salt monohydrate stands for a crystalline form of disodium 3-pyridyl-1-hydroxyethylidene-1,1-bisphosphonate which contains from 4.5 to 6.5% of water and from 13 to 15% of sodium based on the anhydrous salt.

The term risedronate trisodium salt trihydrate stands for a crystalline form of trisodium 3-pyridyl-1-hydroxyethylidene-1,1-bisphosphonate which contains from 12 to 14% of water and from 19 to 21% of sodium based on the anhydrous salt.

If not specified otherwise, all the percentage data herein are given in weight percents.

Our invention concerns sodium 3-pyridyl-1-hydroxyethylidene-1,1-bisphosphonate (sodium risedronate) in so-far-undocumented crystalline forms. More specifically, they are hydrates which contain 6.4 up to 22% of sodium and simultaneously 15 up to 23% of crystalline water if the sodium content is lower than 7.5%, or 4.5 up to 18% if the sodium content is higher than 7.5%.

An useful example of such a hydrate is a modification that is characterized by water content 20 up to 23%, specially with 22.8 w. % of water, and sodium content 5.5 up to 7.5%, specially 6.4 up to 6.7 w. %. The specified water content is built in the crystal lattice and the mentioned crystalline modification is thermodynamically stable. By drying with several different drying regimes, the mentioned crystalline modification was dried to the water content corresponding to the pentahemihydrate, the monohydrate and the anhydrous form of sodium 3-pyridyl-1-hydroxyethylidene-1,1-bisphosphonate. When the substance is left standing on the air, the water content stabilizes spontaneously at the original level. Time that it takes for the water content to stabilize depends on relative humidity in the environment in which the dried substance is placed. It ranges from 2 up to 12 hours for the substance dried to the pentahemihydrate level and from 2 hours up to 12 days for the substance dried to the monohydrate level.

The mentioned new crystalline form is also characterized by better solubility in 0.1 N hydrochloric acid (pH 1.1), which is advantageous for biological availability of the substance.

The new crystalline form was further characterized by a powder X-ray diffraction pattern, infrared spectroscopy, CP-MAS NMR in solid phase and thermogravimetric analysis.

A preferable structure of the hydrate is characterized by the diffraction pattern with interplanar distances d approximately 16.3; 13.0; 9.1 and 4.9 Å.

A different characteristic is provided by the infrared spectrum with bands 1169; 1060; 1046 and 891 cm$^{-1}$.

The thermogravimetric analysis of a preferable composition yields the inflexion point at temperature about 173° C.

Another characteristic of a preferable structure of the hydrate having the given composition is 31P CP-MAS NMR spectrum, which yields signals 13.7 and 20.0 ppm. With this doublet, it significantly differs from previously known pentahemihydrate, which yields the corresponding singlet with a shift of about 15.9 ppm.

Sodium risedronate hydrate containing 12 up to 14% of water and 19 up to 21% of sodium based on the anhydrous salt is another substance having preferable characteristics. When this substance is dried at different conditions and subsequently left to stand in an environment with high relative humidity, the water content also stabilizes at the given value in a period ranging from 2 hours up to 12 days, but mostly in less than 12 hours. Accordingly, this modification is also stable in a humid environment.

A preferable structure of the substance is characterized by the infrared spectrum with bands of approximately 1114; 1085; 956; 616 and 544 cm$^{-1}$.

Risedronate disodium salt monohydrate that contains 4.5 up to 6.5% of water and 13 up to 15% of sodium based on the anhydrous salt is another preferred substance. When this substance is dried at different conditions and subsequently left to stand in an environment with high relative humidity, the water content also stabilizes at the given value in a period ranging from 2 hours up to 12 days, but mostly in less than 12 hours. Accordingly, this modification is also stable in a humid environment.

A preferable structure of the substance is characterized by the infrared spectrum with bands of approximately 1183; 1158; 1071 and 1042 cm$^{-1}$.

Preparation of hydrates of sodium salts of 3-pyridyl-1-hydroxyethylidene-1,1-bisphosphonate in new crystalline forms consists in preparing an aqueous solution of sodium 3-pyridyl-1-hydroxyethylidene-1,1-bisphosphonate, heating the solution to temperature 50 up to 80° C., and pouring it into an overcooled organic solvent, especially one from the group of simple alcohols from the $C_1$ to $C_5$ series, particularly 2-propanol. It is advantageous to use seeding with several small crystals of the appropriate hydrate.

Thanks to their stability in humid environment, these new hydrates of the sodium salts of 3-pyridyl-1-hydroxyethylidene-1,1-bisphosphonic acid are useful as an active substance for treatment of diseases associated with bone-resorption disorders. These diseases include above all osteoporosis, both that associated with a hormonal change in a certain stage of women's lifes and that induced by using various preparations.

An oral dosage form, especially in the tablet form, is a preferred one for using these hydrates. Besides the active substance, suitable diluents, binders, disintegrants and sliding agents are used for producing the tablet.

A directly compressible blend wherein a mixture of mannitol and microcrystalline cellulose plays the role of a diluent is an extraordinarily suitable combination. This combination shows exceptional stability, especially in a humid environment.

EXAMPLES

Water content in the substance was determined using a method according to Karl Fischer and TGA analyses. Sodium content in the substance was determined using acidobasic titration and AAS. Solubility tests were performed according to the Technical Guide European Pharmacopeia.

Example 1

Monohydrate of 3-pyridyl-1-hydroxyethylidene-1,1-bisphosphonic acid is dissolved in a 30-fold volume of distilled water containing one equivalent of sodium hydroxide. The solution is heated to 80° C. and at one bout poured into a 120-fold volume of 2-propanol cooled to temperature −7 up to −10° C. After mixing, temperature of the solution climbs to about +7° C. Within 5 minutes, the emergent suspension cools down to −1° C. The emergent suspension is kept at this temperature for 4 hours. The product is isolated using filtration and it is air dried.

Figure 1:
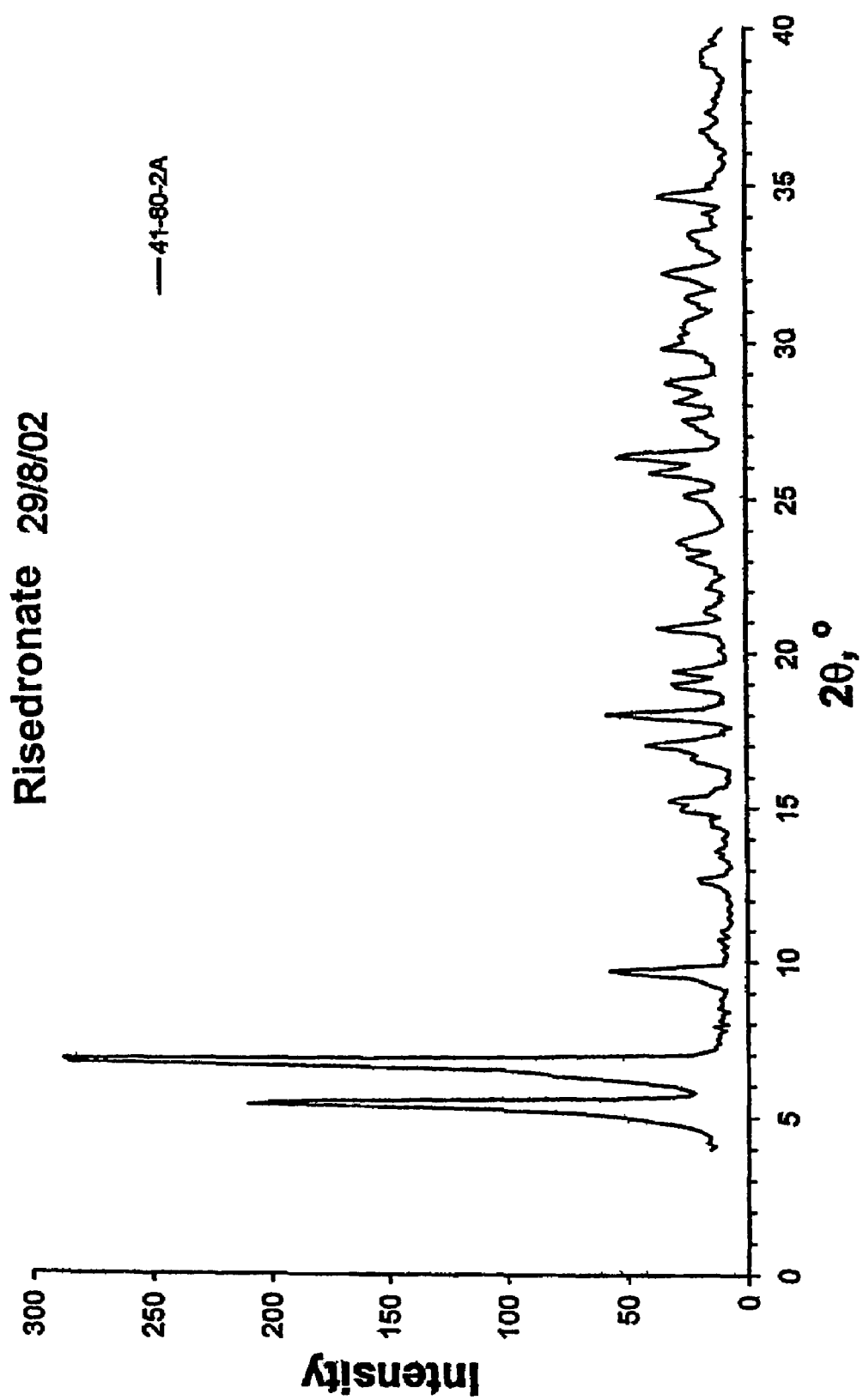
FIG. 1 represents an XR diffraction pattern of risedronate monosodium salt pentahydrate.
Figure 2:
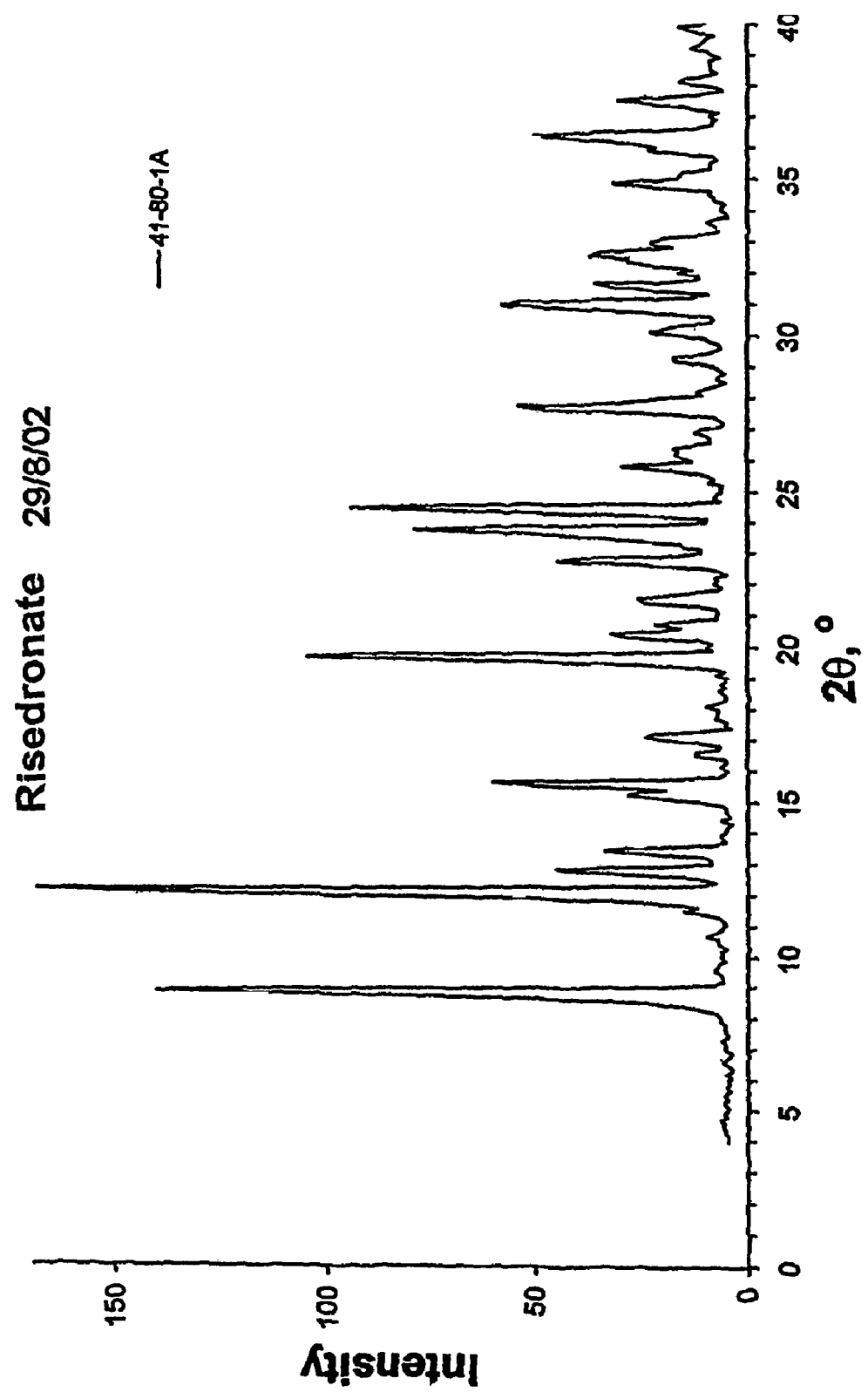
FIG. 2 represents a comparative XR diffraction pattern of risedronate monosodium salt pentahemihydrate.
Figure 3:
FIG. 3 represents a TGA of pentahydrate of monosodium salt of risedronate.
Figure 4:
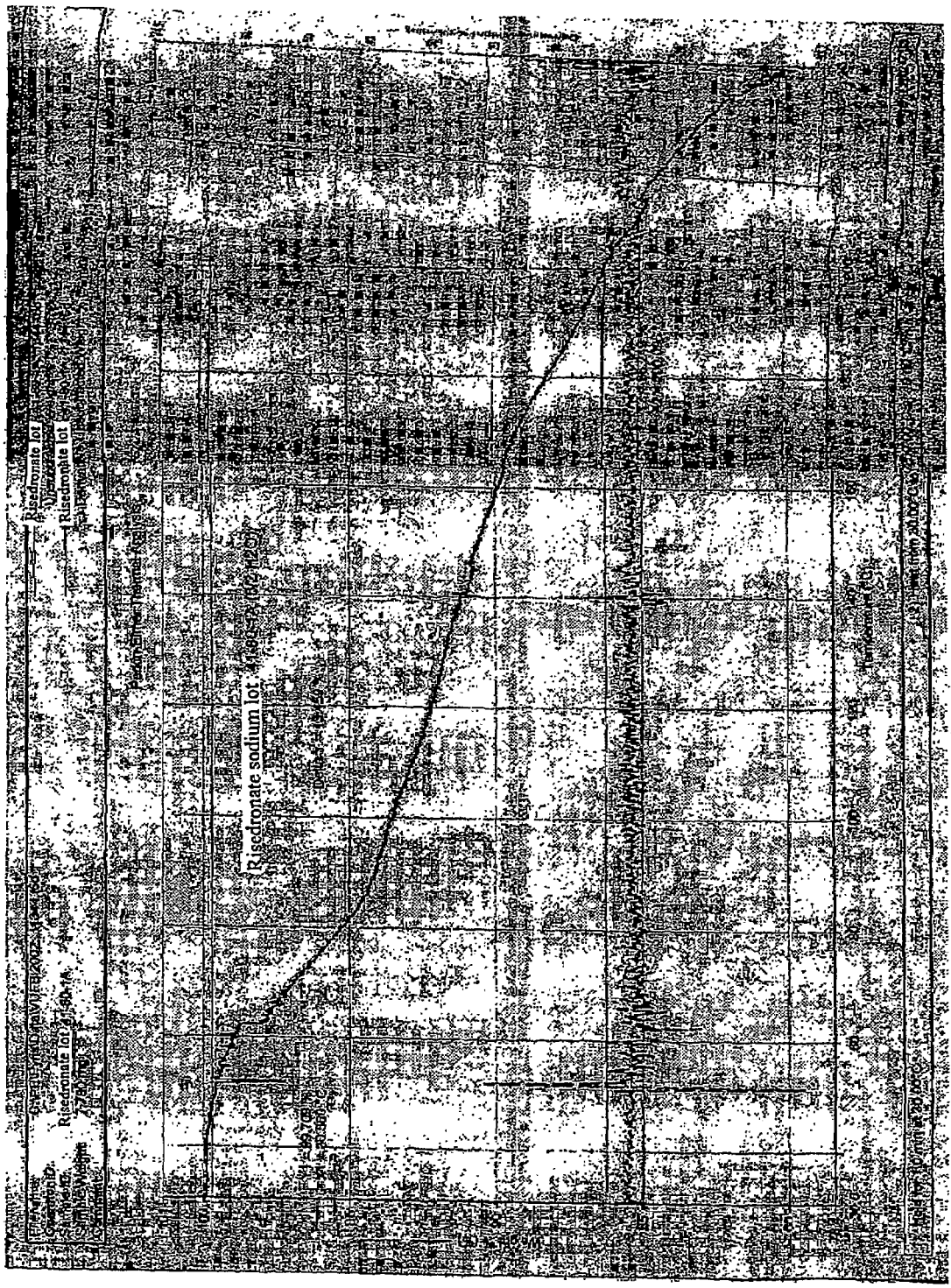
FIG. 4 represents a comparative TGA of risedronate monosodium salt pentahemihydrate.
Figure 5:
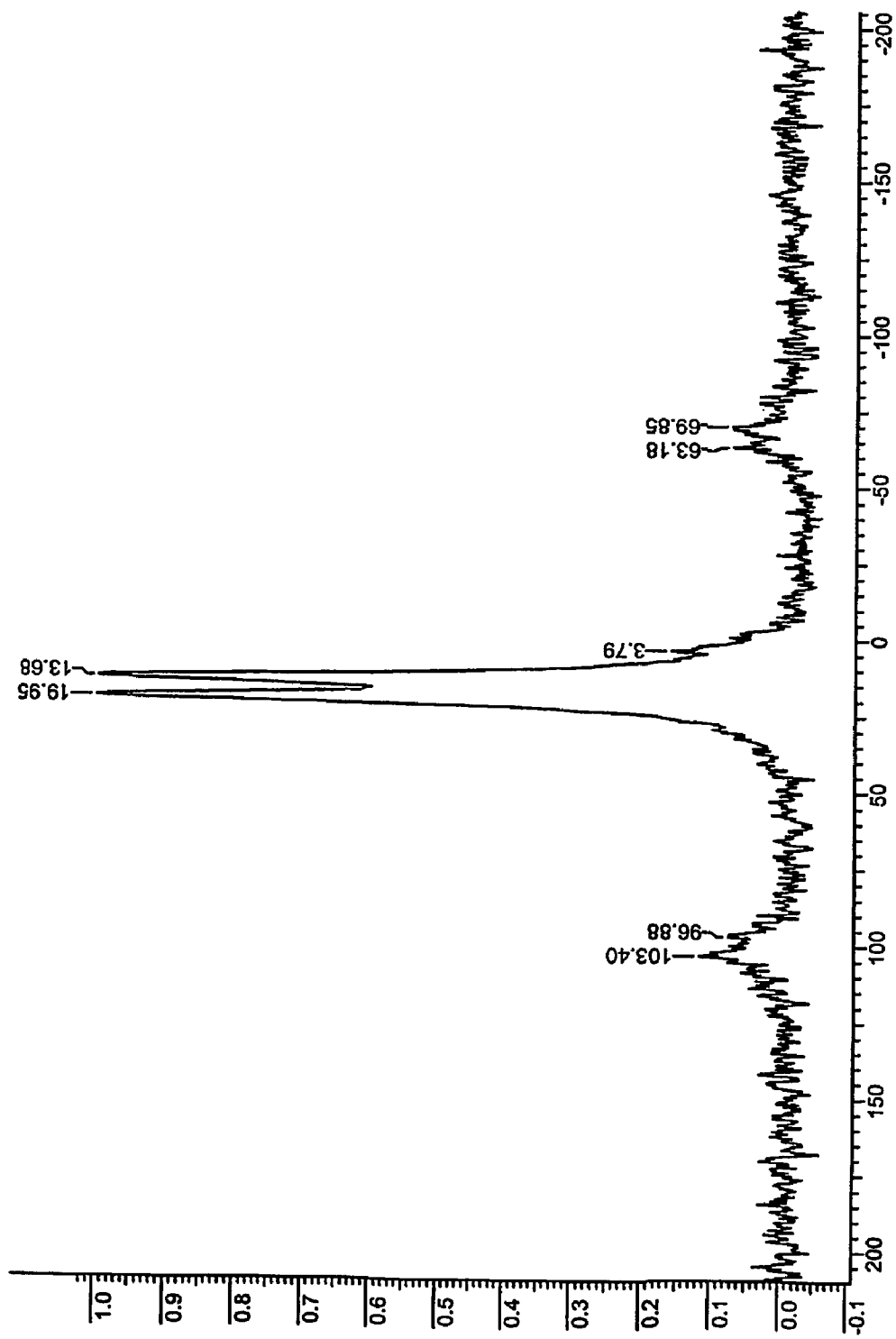
FIG. 5 represents a $^{31}$P CP-MAS NMR spectrum of risedronate monosodium salt pentahydrate.
Figure 6:
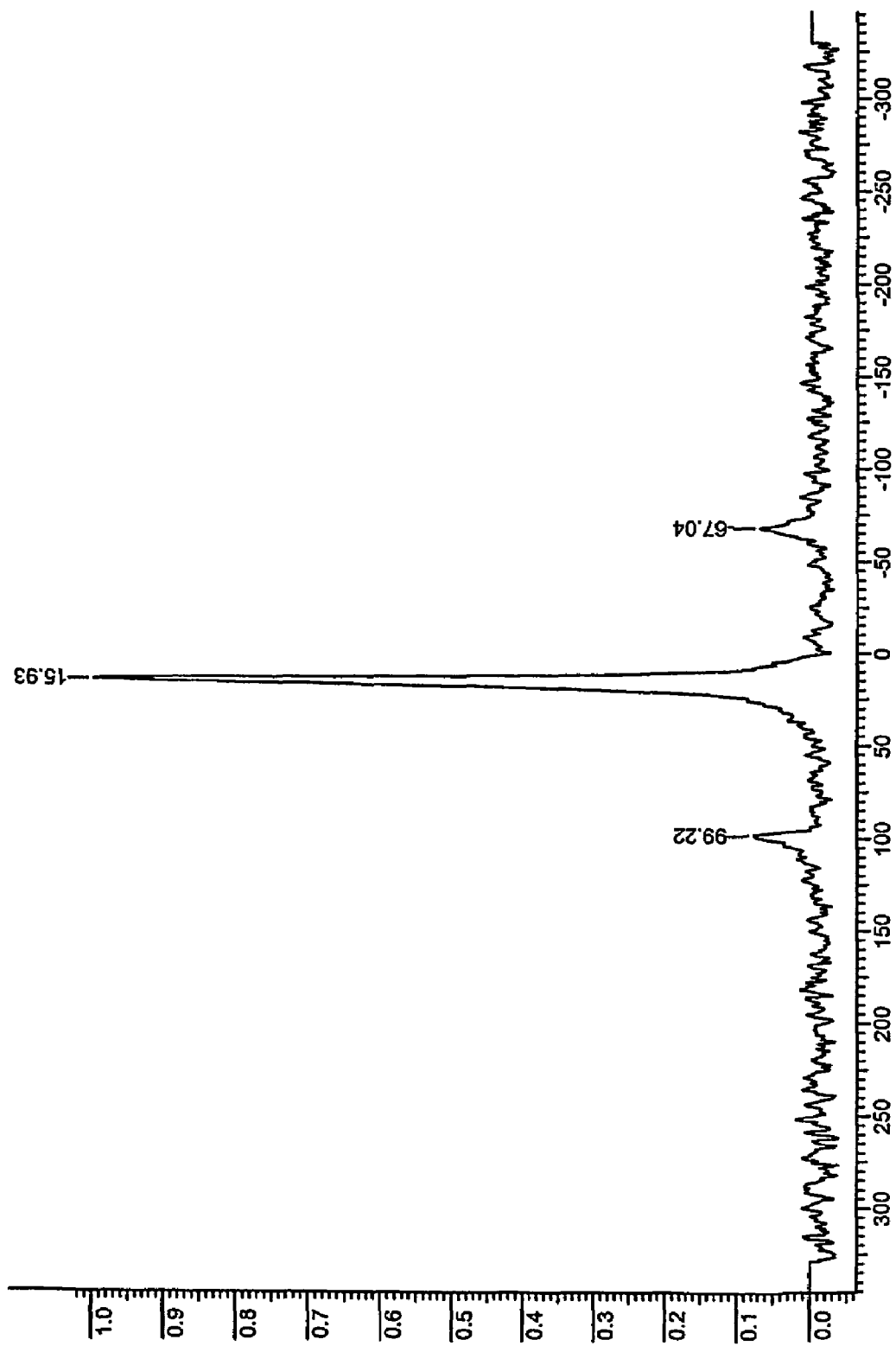
FIG. 6 represents a comparative $^{31}$P CP-MAS NMR spectrum of risedronate monosodium salt pentahemihydrate.
Figure 7:
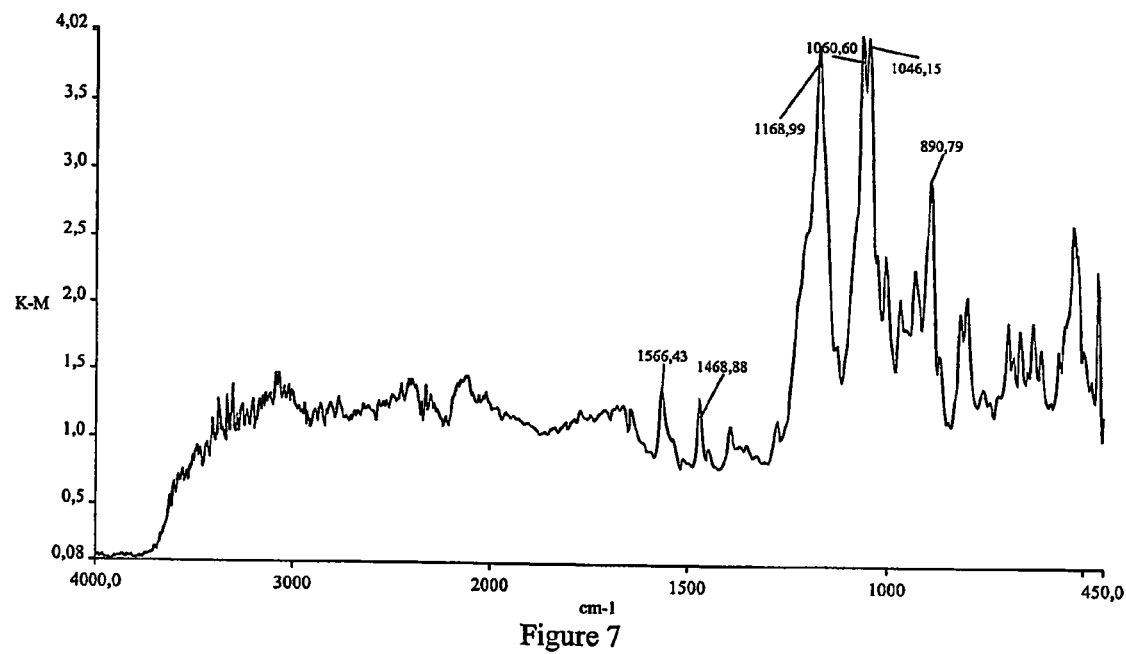
FIG. 7 represents an IR spectrum of risedronate monosodium salt pentahydrate.
Figure 8:
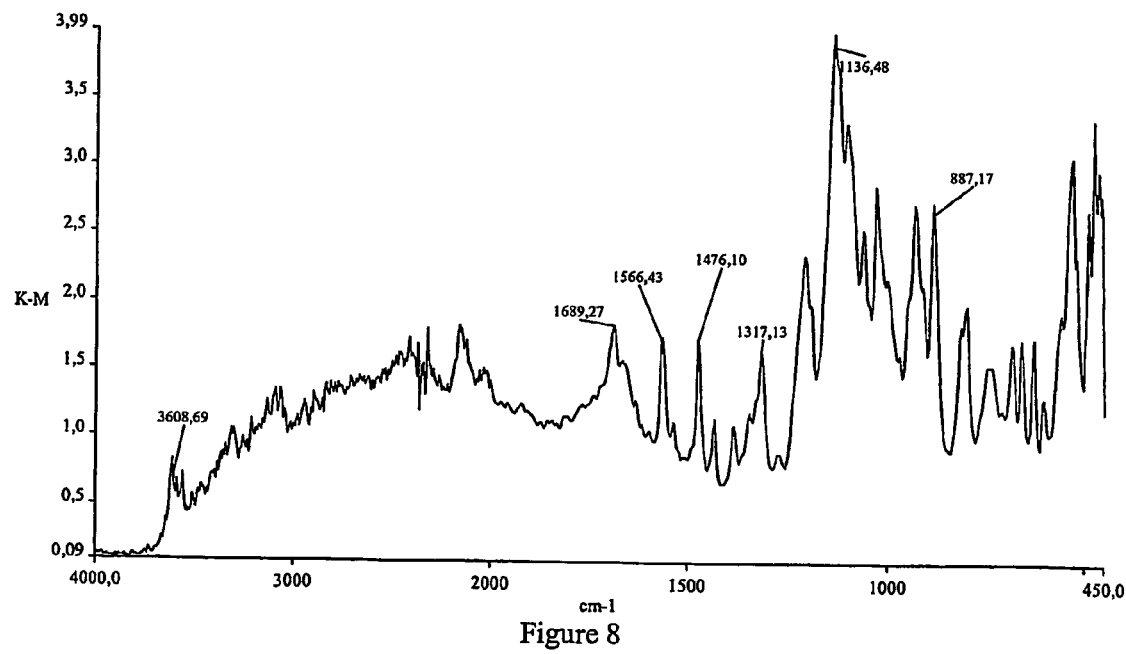
FIG. 8 represents a comparative IR spectrum of risedronate monosodium salt pentahemihydrate.

According to the KF test, the product contains approximately 22.8 weight % of water. Sodium AAS analysis recalculated to dry basis demonstrated that the product contains 6.6 weight % of sodium. The prepared substance yielded the diffraction pattern depicted in FIG. 1 and the $^{31}$P CP-MAS NMR spectrum depicted in FIG. 5.

Example 2

In risedronate monosodium salt pentahydrate (water content about 22.8 weight %) dried in a vacuum oven at 50° C., the substance's water content decreases to 11.5% after six hours. The dried product is hygroscopic. If the substance is left standing at room temperature and usual relative air humidity, the water content returns to the original level within 12 hours.

Example 3

In the pentahydrate dried in a vacuum oven at 105° C., the substance's water content decreases to 3% after six hours. The dried product is hygroscopic. If the substance is left standing at room temperature and usual relative air humidity, the water content increases with a speed of about 0.5% an hour. Within 11 days, the substance's water content returns to about 20 weight %. If the substance is placed in an environment with 100% relative air humidity, the substance's water content returns to 22.7% within two hours. Such water content is stable and does not change at usual lab conditions.

Example 4

Figure 9:
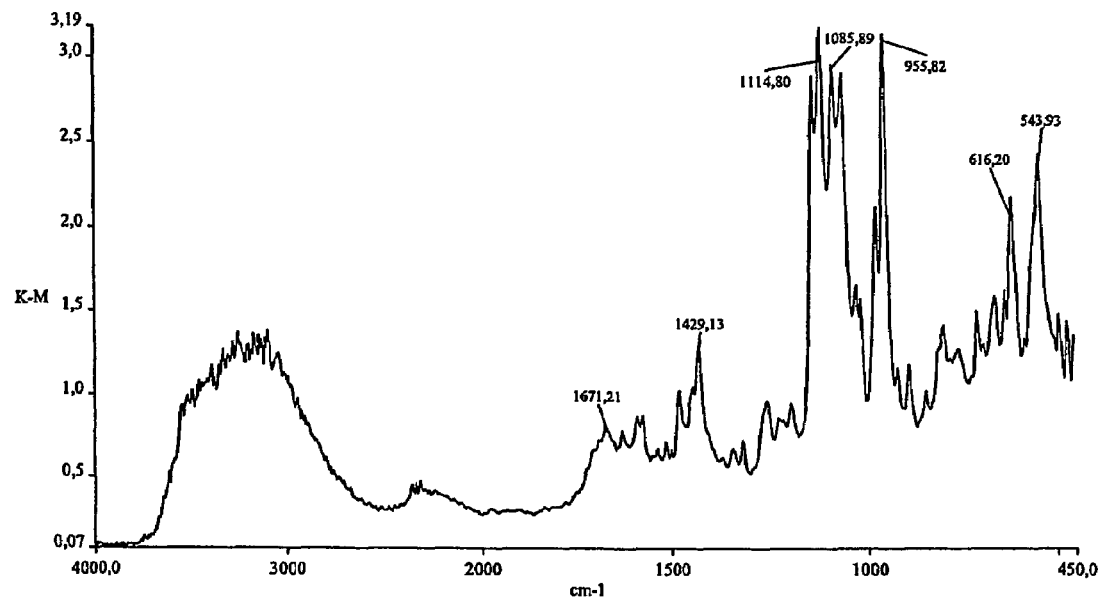
FIG. 9 represents an IR spectrum of risedronate trisodium salt trihydrate.

3-pyridyl-1-hydroxyethylidene-1,1-bisphosphonic acid is dissolved in an aqueous hydroxide solution containing four equivalents of NaOH. The solution is heated to 70° C. and poured into 2-propanol overcooled to temperature −7 up to −10° C. Gradually, a semi-solid milky matter falls out, which disintegrates at temperature of the solvent reflux into a solid white suspension. After filtration and drying in a vacuum oven, one gets the product with 97% yield. Trisodium 3-pyridyl-1-hydroxyethylidene-1,1-bisphosphanate containing about 19.8 weight % of sodium (based on the dry salt) and about 12.7% of water is the product. This amount of contained water corresponds to the trihydrate of trisodium 3-pyridyl-1-hydroxyethylidene-1,1-bisphosphonate. The infrared spectrum of thus obtained substance is depicted in FIG. 9.

When 1 molar equivalent of the trisodium salt is dissolved in water a clear solution is obtained. With addition of two molar equivalents of risedronic acid and heating to 70° C., a clear solution is obtained of the monosodium salt, which is obtained according to example 1 in the new crystalline form containing about 22.8% of water.

Example 5

3-pyridyl-1-hydroxyethylidene-1,1-bisphosphonic acid is dissolved in an aqueous hydroxide solution containing two equivalents of NaOH. The solution is heated to 70° C. and poured into 2-propanol overcooled to temperature −7 up to −10° C. A jelly-like milky matter falls out almost immediately, which disintegrates at temperature of solvent reflux to a solid white suspension. After the suspension is cooled down to the room temperature, the product is isolated using filtration.

Figure 10:
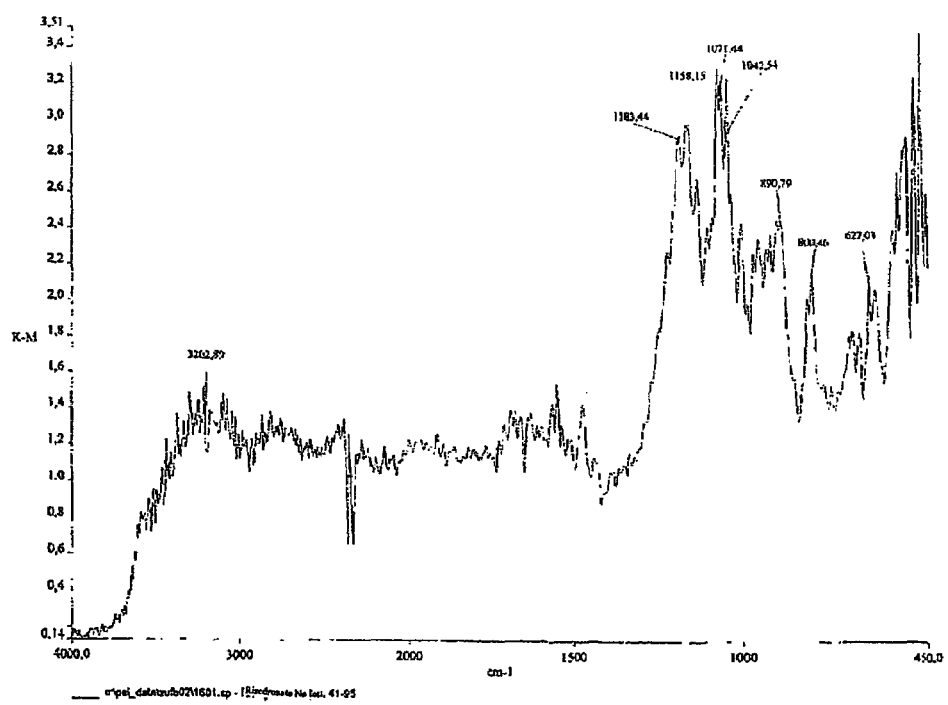
FIG. 10 represents an IR spectrum of risedronate disodium salt monhydrate.

The obtained product contains, after air drying, about 14% of sodium based on the anhydrous substance and about 14% of water. After drying in a vacuum oven, the water content stabilizes at about 5.2%. The substance with this stabilized water content yielded the infrared spectrum depicted in FIG. 10.

Example 6

0.1 ml; 0.9 ml and 2.0 ml of water were gradually added to a 100.25 mg sample of risedronate monosodium pentahemihydrate. The suspension was mixed for about 1 min and tempered to 25° C. for 15 min after each addition of water. At these conditions, the substance was completely dissolved. The proportion of the dissolved substance was determined to be 100% using HPLC.

0.1 ml; 0.9 ml and 2.0 ml of water were gradually added to a 98.78 mg sample of risedronate monosodium salt pentahydrate. The suspension was mixed for about 1 min and tempered to 25° C. for 15 min after each addition of water. At these conditions, the sample of the substance was completely dissolved. The proportion of the dissolved substance was determined to be 100% using HPLC.

Both salts are well soluble in water.

Example 7

0.1 ml; 0.9 ml, 2.0 and 7.0 ml of 0.1 M HCl with pH 1.1 were gradually added to a 106.8 mg sample of risedronate monosodium salt pentahemihydrate. The suspension was mixed for 1 min and tempered to 25° C. for 15 min after each addition of acid. The sample did not dissolve completely. The proportion of the dissolved substance was determined to be 9.46% using HPLC. Accordingly, by dissolving risedronate monosodium salt pentahemihydrate in 0.1 M HCl one gets a solution having the concentration of the active component 874 mg/l.

0.1 ml; 0.9 ml, 2.0 and 7.0 ml of 0.1 M HCl with pH 1.1 were gradually added to a 99.07 mg sample of risedronate monosodium salt pentahydrate. The suspension was mixed for 1 min and tempered to 25° C. for 15 min after each addition of acid. The sample did not dissolve completely. The proportion of the dissolved substance was determined to be 31.62% using HPLC. Dissolving risedronate monosodium salt pentahydrate in 0.1 M HCl yields a solution with concentration of the active component 2418 mg/l.

This experiment demonstrates that the pentahydrate form of risedronate monosodium salt is significantly more soluble in 0.1M hydrochloric acid than the pentahemihydrate form of risedronate monosodium salt.

Example 8

In trihydrate of the trisodium salt dried in a vacuum oven at 105° C., the substance's water content decreases to 1.1% after 6 hours. The dried product is hygroscopic. If the substance is placed in an environment with 100% relative air humidity, the water content returns to the original level within two hours. Such water content is stable and does not change at usual lab conditions.

Example 9

In trihydrate of the disodium salt dried in a vacuum oven at 105° C., the substance's water content decreases to approximately 1.7% after 6 hours. The dried product is hygroscopic. If the substance is placed in an environment with 100% relative air humidity, the water content returns to the level of approximately 5.2% within two hours. Such water content is stable and does not change at usual lab conditions.

Example 10

Monohydrate of 3-pyridyl-1-hydroxyethylidene-1,1-bisphosphonic acid is dissolved in a 10-fold volume of distilled water containing one equivalent of sodium hydroxide. The solution is heated to 80° C. and a 3-fold volume of warm 2-propanol is added. The solution is left to cool spontaneously to ca 62° C. and a small amount of seeding crystals of risedronate monosodium salt pentahydrate is added and the emerging suspension is left to fall out spontaneously. The product is filtrated off at temperature of the mixture 0° C. The product is air dried.

Using the KF test, the product contains approximately 22.8 weight % of water. Sodium AAS analysis recalculated to dry basis demonstrated that the product contains 6.6 weight % of sodium.

Example 11

Monohydrate of 3-pyridyl-1-hydroxyethylidene-1,1-bisphosphonic acid is dissolved in a 10-fold volume of distilled water containing one equivalent of sodium hydroxide. The solution is heated to 60° C. and filtered through a layer of kieselguhr. The filtrate is cooled down to 0° C. and is seeded with the required hydrate. A 2.5-fold volume of 2-propanol, cooled down to a temperature about −17° C., is added to the seeded solution. The temperature of the solution after admixing rises to ca +7° C. Within 5 minutes the emerging suspension is cooled down to 0 to 5° C. The resulting suspension is maintained at this temperature for 4 hours. The product is isolated by filtration and air dried.

Using the KF test, the product contains 20 weight % of water.

Example 12

Monohydrate of 3-pyridyl-1-hydroxyethylidene-1,1-bisphosphonic acid is suspended in a 10-fold volume of distilled water. The suspension is heated to 60° C. and pH is adjusted to 4.09 by means of NaOH. The resulting solution is filtered through a layer of kieselguhr. The filtrate is cooled down to 0° C. and a 2.5-fold volume of 2-propanol, cooled down to a temperature about +7° C., is added. Within 5 minutes the emerging suspension is cooled down to 0 to 5° C. The resulting suspension is maintained at this temperature for 4 hours. The product is isolated by filtration and air dried.

Using the KF test, the product contains 19 weight % of water.

The invention claimed is:

1. A crystalline, hydrated form of a sodium salt of 3-pyridyl-1-hydroxyethylidene-1,1-bisphosphonic acid, wherein:
   the form is a pentahydrate of a monosodium salt of 3-pyridyl-1-hydroxyethylidene-1,1-bisphosphonic acid;
   the form contains from 20 to 23 weight % of water built in the crystal lattice based on the anhydrous salt; and
   the form contains from 5.5 to 7.5 weight % of sodium based on the anhydrous salt.

2. The crystalline form according to claim 1, wherein the form comprises:
   22.8 weight % of water built in its crystal lattice based on the anhydrous salt; and
   from 6.4 to 6.7 weight % of sodium based on the anhydrous salt.

3. The crystalline form according to claim 1 or claim 2, wherein the form shows a powder X-ray diffraction pattern with interplanar distances d that are approximately 16.3; 13.0; 9.1 and 4.9 Å.

4. The crystalline form according to claim 1 or claim 2, wherein the form shows an infrared spectrum having bands at 1169; 1060; 1046 and 891 cm$^{-1}$.

5. The crystalline form according to claim 1 or claim 2, wherein a thermogravimetric analysis of the form shows a plateau at temperature of about 173° C.

6. The crystalline form according to claim 1 or claim 2, wherein a $^{31}$P CP-MAS NMR spectrum of the form shows signals 13.7 and 20.0 ppm.

7. A method of manufacturing the crystalline form according to claim 1, comprising incorporating an aqueous solution of the sodium salt of 3-pyridyl-1-hydroxyethylidene-1,1-bisphosphonic acid heated to a temperature of from 50 to 80° C. into an organic solvent.

8. The method according to claim 7, wherein the organic solvent is selected from the group consisting of simple alcohols from the $C_1$ to $C_5$ series.

9. A method of manufacturing the crystalline form according to claim 1, comprising:
   introducing seeding crystals of a respective hydrate of the sodium salt of 3-pyridyl-1-hydroxyethylidene-1,1-bisphosphonate into a solution of the sodium salt of 3-pyridyl-1-hydroxyethylidene-1,1-bisphosphonic acid; and
   slowly cooling the solution.

10. The method according to claim 9, wherein crystallization is performed from a solution of the sodium salt in a mixture of water and a water-miscible organic substance.

11. The method according to claim 7, wherein the organic solvent is 2-propanol.

* * * * *